(12) United States Patent
Pattee et al.

(10) Patent No.: US 6,470,519 B1
(45) Date of Patent: Oct. 29, 2002

(54) MEDICAL TABLE BRAKE

(75) Inventors: Jeffrey W. Pattee, Salt Lake City, UT (US); David M. Robbins, Sandy, UT (US); Brett A. Karaus, Salt Lake City, UT (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 155 days.

(21) Appl. No.: 09/688,523

(22) Filed: Oct. 16, 2000

(51) Int. Cl.⁷ .................. A61G 13/02; A61G 13/10
(52) U.S. Cl. .................. 5/600; 5/943; 188/31; 188/69; 188/82.74
(58) Field of Search .................. 5/601, 600, 943; 188/31, 82.74, 82.7, 69; 378/209

(56) References Cited

U.S. PATENT DOCUMENTS

| | | | |
|---|---|---|---|
| 4,773,637 A | * | 9/1988 | Jarin .................. 5/600 |
| 4,944,500 A | * | 7/1990 | Mueller et al. .................. 5/600 |
| 5,596,779 A | * | 1/1997 | Meek .................. 5/601 |

FOREIGN PATENT DOCUMENTS

| | | |
|---|---|---|
| DE | 4126170 A1 | 8/1991 |
| EP | 0457248 A3 | 5/1991 |
| EP | 0457248 A2 | 5/1991 |

* cited by examiner

*Primary Examiner*—Alexander Grosz
(74) *Attorney, Agent, or Firm*—McAndrews, Held & Malloy, Ltd.; Peter J. Vogel; Michael A. Dellapenna

(57) ABSTRACT

A brake for a medical table (20) includes a speed detector (40) for determining when the table speed is greater than a threshold value. If the table is moving at greater than the threshold value, the brake is prevented from engaging to prevent the patient from being jolted. When the brake is engaged, teeth (91–95) of a brake tooth member (90) mesh with a groove set assembly (70). The teeth have central planes (A). Each of the teeth has sidewalls that define planes (P1 and P2) which make acute angles with respect to the respective central planes. A position detector (110) warns an operator when the brake is not engaged. A linear bearing assembly (125) guides the brake into the engaged position. A pawl assembly (100) hold the brake in the engaged position until released.

16 Claims, 2 Drawing Sheets

MEDICAL TABLE BRAKE

BACKGROUND OF THE INVENTION

This invention relates to motion control for medical tables, and more particularly relates to brakes for such tables.

Typical table brakes for tilting medical tables utilize spring-loaded teeth that interlock. The teeth have straight walls that should not disengage when the table is tilted. However, the teeth are difficult to disengage if the operator exerts pressure on the table. In addition, the teeth are difficult to disengage if the table is not quite level. Also, the teeth tend to skip if the operator attempts to engage the brake while the table is moving. If the teeth do engage while the table is moving at high speed, the patient is jolted. In addition, prior tables employ no safety interlocks to warn the operator and prevent table motion if the brake is not engaged. Thus, prior tables have a tendency to result in a runaway table, which is very dangerous for the patient and attending personnel. The present invention addresses these problems and provides a solution.

BRIEF SUMMARY OF THE INVENTION

The preferred embodiment is useful in connection with a medical table including a base supporting a tabletop suitable for supporting a patient. In order to help position the patient, the top is movable with respect to the base. In such an environment, the table motion can be controlled with a brake comprising a groove set. At least one brake tooth is movable relative to the groove set to a first brake tooth position of engagement with said groove set and is movable to a second brake tooth position of disengagement with said groove set. A pawl is movable to a first pawl position to maintain the engagement of the groove set with the brake tooth and is movable to a second pawl position to enable disengagement of the groove set from the brake tooth. A switch generates a first signal in response to actuation by an operator of the table. An actuator is responsive to the first signal to cause the brake tooth to move to the second brake tooth position and to cause the pawl to move to the second pawl position, whereby the operator can move the table relative to the base. A position detector provides warning when the brake tooth is out of the first brake tooth position. A connector couples the groove set to one of the table and base and couples the brake tooth, pawl, and actuator to the other of the table and base.

By using the foregoing features, the table can be locked relative to the base with a degree of ease, safety and convenience previously unattained.

DETAILED DESCRIPTION OF THE INVENTION

Figure 1:
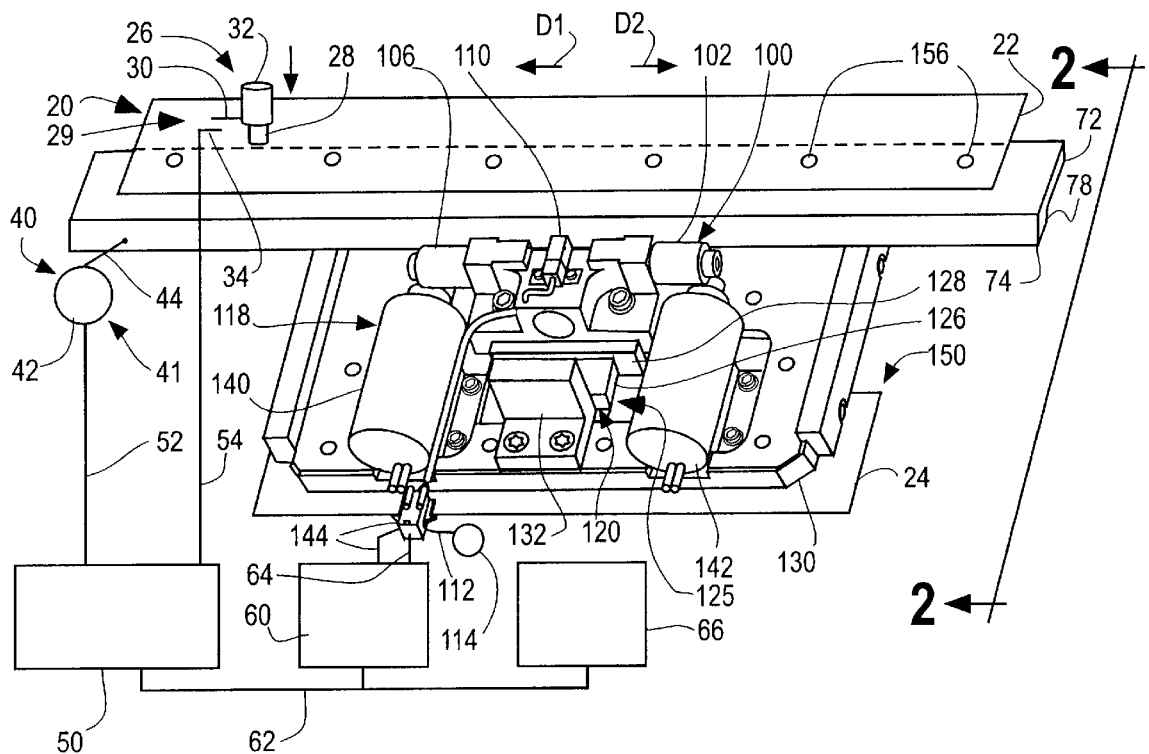
FIG. 1 is an isometric view of a preferred form of the invention shown with a fragment of an exemplary medical tabletop and base and a block diagram of a preferred form of a speed detector forming a portion of the preferred embodiment.

In general, the preferred embodiment may be used to brake a medical table. The brake utilizes a brake tooth member employing teeth that are cut at an angle, which helps to separate (disengage) them even if there is a side load on the teeth. Also, the brake tooth member is carried by a carriage employing a linear ball bearing that reduces friction of the sliding teeth. The tapered teeth are held in their engaged position by a latch using a pawl that prevents tooth separation after the teeth catch to prevent the teeth from excessive skipping if brake engagement is attempted while the table is in motion. There also is table velocity sensing that actually prevents the brake from engaging while the table is moving above a threshold speed that is set by software. Limiting the engagement velocity prevents excessive jolts to the patient and damage to the mechanism. A position-sensing device is also present to prevent table motion and warn the operator that the brake is not engaged.

More specifically, referring to the drawings, the preferred embodiment may be used to control motion of a medical table 20. The preferred embodiment basically comprises a handle assembly 26, including a switch assembly 29, speed detector 40, a groove set assembly 70, a brake tooth member 90, a pawl or latch assembly 100, a position detector 110, an actuator assembly 118, and a connector assembly 150.

Referring to FIG. 1, table 20 includes a top 22 movable in opposed directions D1 and D2 that may be parallel with the longitudinal axis of the table and parallel to the spine of a reclining patient placed on the table. Top 22 moves relative to a base 24, which may be movable over a floor or which may be attached to the floor. Only a fragment of top 22 and base 24 are shown schematically in FIG. 1.

Handle assembly 26 is incorporated into top 22 and is made to fit into the hand of an operator of the table. In order to move the table top, the operator grasps a grip 32 and depresses the grip with respect to a handle base 28 on which grip 32 is mounted. Switch assembly 29 is arranged so that a contact 30 makes electrical contact with a contact 34 when grip 32 is depressed by the operator. Grip 32 is spring biased in an upward direction so that contacts 30 and 34 open when the operator releases the handle.

Still referring to FIG. 1, speed detector 40 comprises a string potentiometer 41 that includes a case 42 enclosing a potentiometer (not shown). The potentiometer has its resistance altered by a string 44 that is operated by a coiling mechanism that biases the string inside the case. As the string is pulled from the case, the resistance of the potentiometer changes accordingly. String 44 is connected to tabletop 22 as shown. As top 22 moves in direction D2, string 44 is pulled from case 42. As tabletop 22 moves in direction D1, string 44 is retracted into case 42. The potentiometer is biased electrically to generate signal proportional to the potentiometer resistance, which is conducted over a conductor 52 to an input interface board 50. Switch contact 34 is connected to board 50 over a conductor 54. The operation of board 50 is controlled by a processor 66 in a well-known manner. Processor 66 may be a microprocessor or microcontroller programmed to perform the functions described later in this specification. Such programming is within the skill of ordinary programmers based on the following description. Processor 66 receives signals from board 50 over a bus 62 and generates a speed signal proportional to the velocity of tabletop 22. If top 22 is moving at a velocity greater than a predetermined threshold value, such as three inches per second, processor 66 generates a signal on bus 62 that is transmitted to an output interface board 60. Board 60, in turn, generates a signal on a conductor 64 within a cable 144 that prevents the table from locking in a manner to be described later.

Figure 2:
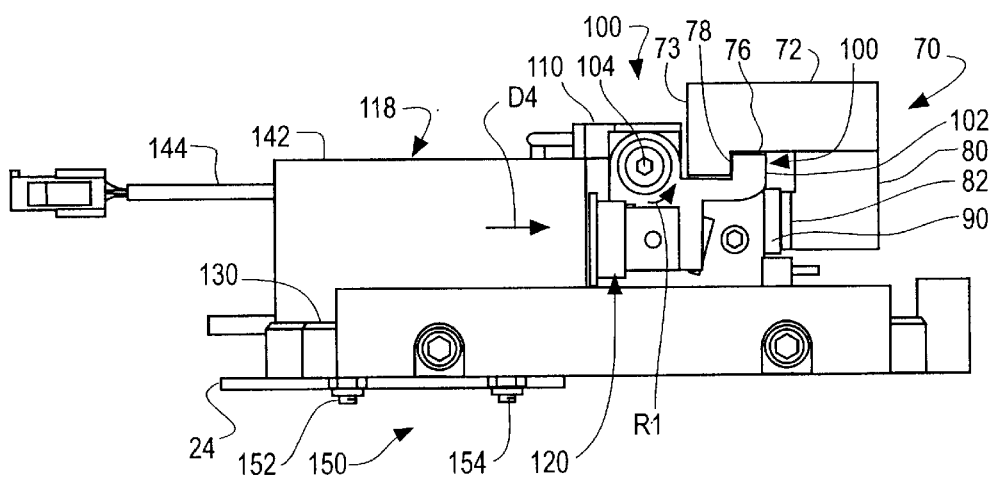
FIG. 2 is a side elevational view of the apparatus shown in FIG. 1 taken along line 2—2 of FIG. 1, with the table top, base and speed detector removed, and showing the pawl and brake tooth member illustrated in FIG. 1 in the engaged position.
Figure 4:
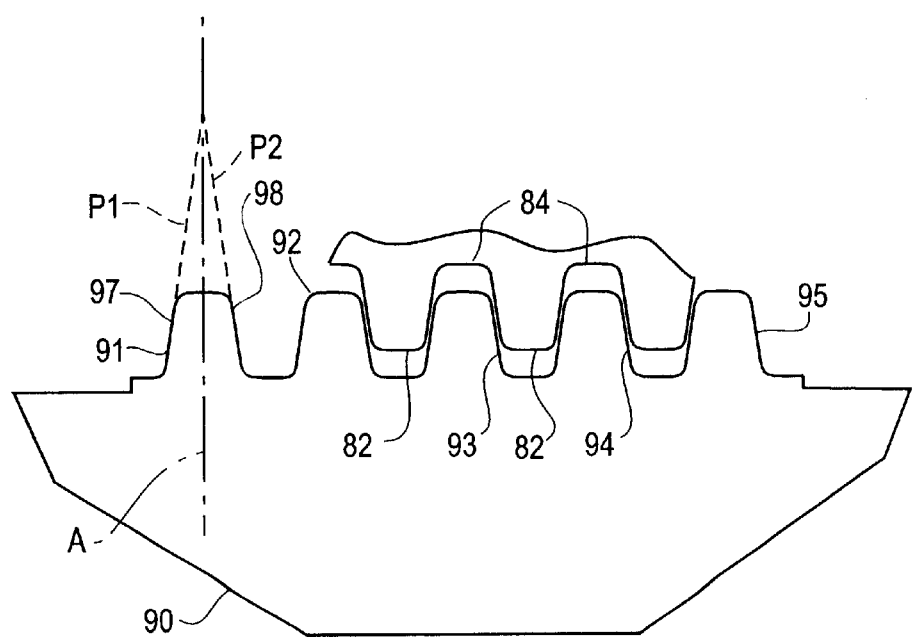
FIG. 4 is an enlarged elevational view of a preferred form of the brake tooth member shown in FIGS. 2 and 3.

Referring to FIGS. 1–2, groove set assembly 70 comprises an L-shaped fence 72, which includes an elbow 74 defining engagement surfaces 76 and 78. Assembly 70 also includes a brake rack 80 connected to fence 72. Referring to FIG. 4, rack 80 includes teeth 82 and grooves 84 as shown. In FIG. 4, the teeth and grooves are shown in an engaged position.

Referring to FIGS. 2 and 4, brake tooth member 90 includes teeth 91–95 shown in the engaged position. Tooth 91 defines a central plane A and includes sidewalls 97 and 98. Sidewall 97 defines a plane P1 that makes an acute angle with respect to plane A, and sidewall 98 defines a plane P2 that makes an acute angle with respect to plane A. The angles that planes P1 and P2 make with plane A are equal. Teeth 92–95 define central planes like plane A, and include side walls like side walls 97 and 98 which define planes like P1 and P2 which make identical angles with their respective central planes.

Referring to FIGS. 1 and 2, pawl assembly 100 comprises a pawl 102 and a pawl 106 that both pivot around an axis of rotation 104. As shown in FIG. 2, pawl 102 engages surfaces 76 and 78 to prevent brake tooth member 90 from moving out of the engaged position shown in FIG. 2. Pawl 106 engages similar surfaces in fence 72. Pawls 102 and 106 are urged to rotate in direction R1 (FIG. 2) by springs (not shown).

Referring to FIGS. 1 and 2, position detector 110 comprises a Hall effect device that generates a signal on conductor 112 when the detector is beyond a predetermined distance from a face 73 of fence 72. The signal causes a light bulb 114 to light, thereby warning the operator that the table is not locked. A switch might be used in lieu of or in addition to the hall effect proximity sensor. The switch would detect pawl position to make sure that pawls 102 and 106 are engaged. A photoelectric sensor also could be used to sense the position of pawls 102 and 106.

Figure 3:
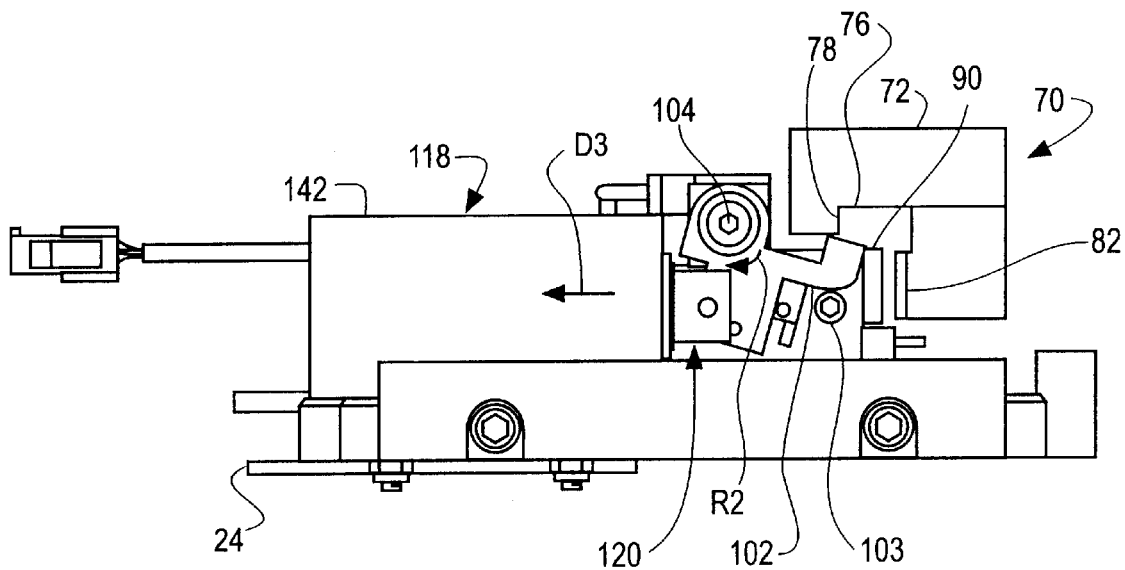
FIG. 3 is a side elevational view like FIG. 2 taken along line 2—2 of FIG. 1 showing the pawl and brake tooth member in the disengaged position.

Referring to FIGS. 1 and 2, actuator assembly 118 includes a carriage 120 that supports brake tooth member 90, pawl assembly 100 and position detector 110. Carriage 120 moves with respect to a base plate 130 on a linear bearing assembly 125 that includes linear bearing slide 128 guided on a linear bearing rail 126. Slide 128 includes a linear bearing (not shown). A pair of springs (not shown) urges the carriage to move in direction D4 (FIG. 2) into an engaged position shown in FIG. 2. In the engaged position, groove set assembly 70 and brake tooth member 90 engage as shown in FIG. 4. When carriage 90 is driven in direction D3, pawls 102 and 106 are rotated in direction R2 (FIG. 3). The movement of pawl 102 in direction R2 is limited by a stop 103. The movement of pawl 106 is limited by a similar stop.

Base plate 130 supports a stop 132 that limits the movement of the carriage in direction D3 (FIG. 3). Base plate 130 supports solenoids 140 and 142 that are connected by a cable 144 to interface board 60. The plungers of the solenoids are mechanically coupled to carriage 120. Carriage 120 is centrally located between solenoids 140 and 142.

Connector assembly 150 couples base plate 130 to table base 24 with bolts, such as 152 and 154 shown in FIG. 2. Only a fragment of table base 24 is shown in FIG. 2. Connector assembly 150 also couples fence 72 to table top 22 with bolts that pass through holes shown as 156 in FIG. 1.

The operation will be explained assuming that table top 22 is locked by having groove set assembly 70 and brake tooth member 90 in the engaged position shown in FIG. 2. In the engaged position, assembly 70 and member 90 engage each other as shown in FIG. 4, and pawl 102 engages surfaces 76 and 78 as shown. (Pawl 106 engages similar surfaces.) If the operator wants to move tabletop 22, he depresses grip 32 to close switch 29. In response to the closure of switch 29, processor 66 causes solenoids 140 and 142 to energize, thereby driving carriage 120 in direction D3 (FIG. 3). As a result, pawls 102 and 106 are rotated in direction R2 and disengage from surfaces 76 and 78 which frees carriage 90 to move in direction D3 to the disengaged position shown in FIG. 3. In the disengaged position, groove set assembly 70 and brake tooth member 90 make no contact so that tabletop 22 is free to move with respect to base 24. When the operator has moved table 22 to the desired position and the table is stopped, or the table velocity is below the threshold value, the operator releases grip 32 and switch 29 opens. When switch 29 is open, processor 66 stops generating the energizing signal for solenoids 140 and 142 and the solenoids deenergize. As a result, carriage 120 is spring driven in direction D4 and the pawls are driven in direction R1 into the engaged position shown in FIG. 2. In the engaged position, groove set assembly 70 and brake tooth member 90 are engaged as shown in FIG. 4, thereby locking table 22 with respect to base 24. If tabletop 22 is moving at a speed greater than the threshold velocity when the operator releases grip 32, processor 66 causes the continued energization of solenoids 140 and 142, thereby preventing carriage 120 from being spring driven in direction D4. Normally the table decreases in speed below the threshold velocity within a short travel distance. At that point in time, processor 66 senses the decrease in table top speed below the threshold velocity, and deenergizes solenoids 140 and 142, thereby releasing carriage 120 for spring driven travel in direction D4 as previously explained.

Those skilled in the art recognize that the preferred embodiments may be altered and modified without departing from the true spirit and scope of the invention as defined in the accompanying claims.

What is claimed is:
1. In a medical table including a base supporting a table top suitable for supporting a patient, said top being movable with respect to said base, a brake system for the table comprising:
   a groove set;
   at least one brake tooth movable relative to the groove set to a first brake tooth position of engagement with said groove set and movable to a second brake tooth position of disengagement with said groove set;
   a pawl movable to a first pawl position to maintain the engagement of the groove set with the brake tooth and movable to a second pawl position to enable disengagement of the groove set from the brake tooth;
   a switch generating a first signal in response to actuation by an operator of the table;
   an actuator responsive to the first signal to cause the brake tooth to move to the second brake tooth position and to cause the pawl to move to the second pawl position whereby the table can be moved relative to the base by the operator;
   a position detector to provide warning when the brake tooth is out of the first brake tooth position; and a connector coupling the groove set to one of the table and base and coupling the brake tooth, pawl, and actuator to the other of the table and base, whereby the table can be locked relative to the base.

2. A brake system, as claimed in claim 1, wherein said brake tooth defines a center plane, wherein said brake tooth comprises a first wall surface defining a first plane making a first angle with said center plane and wherein said brake tooth comprises a second wall surface defining a second plane making a second angle with said center plane.

3. A brake system, as claimed in claim 1, wherein said actuator comprises:

a spring urging said brake tooth into said first position and urging said pawl into said first pawl position; and at least one solenoid responsive to the first signal to cause the brake tooth to move to the second brake tooth position and to cause the pawl to move to the second pawl position.

4. A brake system, as claimed in claim 1, wherein the actuator comprises:

a mounting plate;

a carriage carrying the pawl and the brake tooth; and a linear bearing for moving the carriage with respect to the mounting plate.

5. A brake system, as claimed in claim 4 wherein the at least one solenoid comprises a pair of solenoids and wherein the carriage and linear bearing are positioned between the pair of solenoids.

6. A brake system, as claimed in claim 1, and further comprising a speed detector generating a speed signal proportional to the relative speed between the table and the base wherein the actuator urges the brake tooth into the second brake tooth position and urges the pawl into the second pawl position in response to a speed signal greater than a predetermined value.

7. A brake system, as claimed in claim 6, wherein the speed detector comprises a processor responsive to the speed signal.

8. A brake system, as claimed in claim 7, wherein the speed detector comprises a string potentiometer for generating the speed signal.

9. A brake system, as claimed in claim 8, wherein the string potentiometer comprises a string responsive to movement of the table.

10. A brake system, as claimed in claim 1, wherein the at least one brake tooth comprises a plurality of brake teeth.

11. A brake system, as claimed in claim 1, wherein the groove set is coupled to a fence and wherein the pawl engages the fence when the pawl is in the first pawl position.

12. A brake system, as claimed in claim 11, wherein the position detector detects the proximity of the fence.

13. A brake system, as claimed in claim 12, wherein the position detector comprises a Hall effect device.

14. A brake system, as claimed in claim 1, wherein the pawl rotates between the first pawl position and the second pawl position.

15. A brake system, as claimed in claim 1, wherein the connector couples the groove set to the table and couples the brake tooth, pawl and actuator to the base.

16. A brake system, as claimed in claim 1, wherein the groove set comprises a set of teeth which mate with the brake tooth.

\* \* \* \* \*